(12) United States Patent
Ekberg et al.

(10) Patent No.: US 7,964,558 B2
(45) Date of Patent: Jun. 21, 2011

(54) THERAPEUTIC APPLICATIONS FOR C-PEPTIDE

(75) Inventors: Karin Ekberg, Stockholm (SE); John Wahren, Stockholm (SE)

(73) Assignee: La JollaCA (US)

( * ) Notice: Subject to any disclaimer, the term of this patent is extended or adjusted under 35 U.S.C. 154(b) by 721 days.

(21) Appl. No.: 10/575,701

(22) PCT Filed: Oct. 13, 2004

(86) PCT No.: PCT/GB2004/004341
§ 371 (c)(1),
(2), (4) Date: Dec. 11, 2006

(87) PCT Pub. No.: WO2005/039627
PCT Pub. Date: May 6, 2005

(65) Prior Publication Data
US 2007/0082842 A1  Apr. 12, 2007

(30) Foreign Application Priority Data

Oct. 13, 2003 (GB) .................................. 0323979.5

(51) Int. Cl.
*A61K 38/28* (2006.01)
*A61K 49/00* (2006.01)
(52) U.S. Cl. ............................................. 514/3; 424/9.1
(58) Field of Classification Search .................. None
See application file for complete search history.

(56) References Cited

U.S. PATENT DOCUMENTS

| | | | |
|---|---|---|---|
| 2002/0077317 A1 | 6/2002 | Das | |
| 2003/0180332 A1 | 9/2003 | Rimpler et al. | |

FOREIGN PATENT DOCUMENTS

| | | | |
|---|---|---|---|
| EP | 0 132 769 A1 | | 2/1985 |
| SE | 460334 B | | 10/1989 |
| WO | WO 98/13384 | | 4/1998 |
| WO | WO/98/13384 | * | 4/1998 |
| WO | WO 02/22211 A2 | | 3/2002 |
| WO | WO 02/38129 A2 | | 5/2002 |

OTHER PUBLICATIONS

Johansson et al., Biochemical and Biophysical Research Communications, 295(5):1035-1040, Aug. 2, 2002.*
Johansson et al., Diabetologia, 39:687-695, 1996.*
Johansson et al., Diabetologia, 35:121-128 (1992).*
Fernqvist-Forbes et al., Diabetologia, 36 (Suppl 1): A1-222, 1993, Abstract 483 on p. A126.*
Linde B., Absorption of C-peptide after subcutaneous injection in type 1 diabetic patients, In: "C-Peptide and type 1 diabetes mellitus", An International Symposium, Karolinska Institute, Stockholm Sweden, Sep. 23-24, 1994.*
Henriksson, M. et al. (2000) "Unordered structure of proinsulin c-peptide in aqueous solution and in the presence of lipid vesicles" *Cell. Mol. Life Sci.* 57:337-342.
Ido, Y. et al. (1997) "Prevention of vascular and neural dysfunction of diabetic rats by c-peptide" *Science* 277:563-566.
Johansson, J. et al. (2002) "Molecular effects of proinsulin c-peptide" *Biochem. Biophys. Res. Com.* 295:1035-1040.
Kamiya, H. et al. (2004) "C-peptide prevents nociceptive sensory neuropathy in type 1 diabetes" *Ann. Neurol.* 56:827-835.
Kitamura, T. et al. (2001) "Proinsulin c-peptide rapidly stimulates mitogen-activated protein kinases in swiss 3t3 fibroblasts: requirement of protein kinase c. phosphoinositide 3-kinase and pertussis toxin-sensitive g-protein" *Biochem. J.* 355:123-129.
Pramanik, A. et al. (2001) "C-peptide binding to human cell membranes: importance of Glu27" *Biochem. Biophys. Res. Com.* 284:94-98.
Rigler, R. et al. (1999) "Specific binding of proinsulin c-peptide to human cell membranes" *PNAS USA* 96:13318-13323.
Shafqat, J. et al. (2006) "Proinsulin c-peptide elicits disaggregation of insulin resulting in enhanced physiological insulin effects" *Cell. Mol. Life Sci.* 63:1805-1811.
Sima, A.A.F. et al. (2001) "C-peptide prevents and improves chronic type 1 diabetic polyneuropathy in the bb/wor rat" *Diabetologia* 44:889-897.
Wahren, J. et al. (2000) "Role of c-peptide in human physiology" *Am. J. Physiol. Endocrinol. Metab.* 278:E-759-E768.
Wahren, J. et al. (2003) "Does c-peptide have a role in the pathophysiology of type 1 diabetes?" Chapter 29 in *International Textbook of Diabetes*, 3rd Ed. Wiley pub., London.
Zhang, W. et al. (2006) "C-peptide improves neuropathy in type 1 diabetic bb/wor-rats" *Diabetes Met. Res. Revs.* Epub ahead of print, 9 pages.
Johansson, B-L et al; C-Peptide and Diabetic Autonomic Neuropathy; Diabetologia (Journal of the European Association for the Study of Diabetes) vol. 39; Num 6; Jun. 1996; pp. 687-695.
Sjoberg, et al., Diabetologia, 34, 423-428, 1991.
Johansson, et al., 1992, Diabetologia, 35, 1151-1158.
Johannsson, et al, 1993, J. Clin. Endocrinol & Meta, 77, 976-981.
Wahren, et al., 1994, Diabetelogia, 37, S2, S99-107.
Wahren, et al., 1996, J. Intern. Med., 240(3), 115-24.
Wu, et al., 1996, Acta Physiol. Scand, 157(2), 253-8.
Johansson, et al., 1996, Diabetologia, 39, 687-695.
Oskarsson, et al., 1997, Diabet Med., 14, 655-659.
Forst, et al., 1998, J. Clin. Invest., 101(10), 2036-41.
Forst,et al., 1998, Exp. Clin. Endocrinal. Diabetes., 106(4), 270-6.
Wahren, et al., 1998, Horm. Metab. Res., 30(1), A2-5.
Li, et al., 1999, Diabetologia, 42(8), 958-64.
Johansson, et al., 1999, Acta Physiol. Scand, 165, 39-44.
Forst, et al., 2000, Clin. Sci., 98(3), 283-90.
Johansson, et al., 2000, Diabetic Med. 17 (3) 181-189.
Sima, et al., Int J. Exp. Diabetic Res., 2(2), 145-51.
Wahren et al., 2001, Curr. Diab. Rep., 1(3), 261-6.
Zhang, et al., 2001, Int. J. Exp. Diabetic Res.
Fernqvist-Forbes, et al., 2001, Acta Physiol. Scand., 172(3), 159-65.
Huang, et al., 2002, Naunyn Schmiedebergs Arch Pharmacol., 365(1), 67-73.
Hansen, et al., 2002, Diabetes.51 3077-3082.
Forst, et al., 2002, Diabetes Care 25(6) 1096-7.
Cotter, et al., 2003, Diabetes, 52(7); 1812-7.
Johannsson, et al., 2003, Am, J. Physiol, Endocrinol., Met 285(4), E864-70.
Wahren, et al., 2003, Diabetes Med. Res. Revs., 19(5), 345-7.
Ekberg, et al., 2003, Diabetes, 52, 536-541.

* cited by examiner

*Primary Examiner* — Daniel E Kolker
*Assistant Examiner* — Stacey MacFarlane
(74) *Attorney, Agent, or Firm* — Dennis A. Bennett

(57) ABSTRACT

The present invention relates to administration of C-peptide in a once daily dose for use in the treatment of diabetes and diabetic complications.

7 Claims, 5 Drawing Sheets

Figure 1A

| Proinsulin | C-peptide |
|---|---|
| Ins_Human | EAEDLQVGQVELGOGPGAGSLQPLALEGSLQ (SEQ ID NO. 1) |
| Ins Pantr (Chimpanzee) | EAEDLQVGQVELGGGPGAGSLQPLALEGSLQ (SEQ ID NO. 9) |
| Ins_Aotr (Night monkey) | EAEDLQVGQVELGGGSITGSLPPLEGPMQ (SEQ ID NO. 10) |
| Ins Macpa (Crabeatingmaoaque) | EAEDPQVGQVELCSGGPGAGSLQPLALEJSLQ (SEQ ID NO. 11) |
| Ins_Cerab (Green monkey) | EAEDPQVGQVELGGGPGAGSLQPLALEGSLQ (SEQ ID NO. 12) |
| Ins Pig | EAENPQAGAVELGGGLGGLQALALEGPPQ (SEQ ID NO. 13) |
| Ins_Boven | EVEGPQVGALELAGGPGAGGLEGPPQ (SEQ ID NO. 14) |
| Ins_Horse | EAEDPQVGEVELGGGPGLGGLQPLALAGPQQ (SEQ ID NO. 15) |
| Ins sheep | EVEGPQVGALELAGGPGAGGLEGPPQ (SEQ ID NO. 16) |
| Ins Canpa (dog) | EVEDLQVRDVELAGAPGEGGLQPLALEGALQ (SEQ ID NO. 17) |
| Ins_Rabbit | EVE LQVGQAELGOGPGAGGLQPSALELALQ (SEQ ID NO. 18) |
| Ins 1_Rat | EVEDPQYPQLEGGPEAGDLQTLALEVARQ (SEQ ID NO. 19) |
| Ins2_Rat | EVEDPQVAQLELGGGPGAGDLQTLALEVARQ (SEQ ID NO. 20) |
| Ins Rodsp (rodent sp) | EVEDPQVGQVELGAGPGAGSEQTLALEVARQ (SEQ ID NO. 21) |
| Insi_mouse | EVEDPQVEQLELGGSPGDLQTLALEVARQ (SEQ ID NO. 22) |
| Ins2_Mouse | EVEDPQVAQLELGGGPGAGDLQTLALEVAQQ (SEQ ID NO. 23) |
| Ins Caypo (guinea pig) | ELEDPQYEQTELGMGLGAGGLQPLALEMALQ (SEQ ID NO. 24) |

Figure 1B

| | |
|---|---|
| Ins_Crib | GYEDPQVAQLELGOGPGADDLQTLALEVAQQ (SEQ ID NO. 25) |
| Ins_Psaob | GYDDPQMPQLELGGSPGAGDLRALALEVARQ (SEQ ID NO. 26) |
| Ins_Ocide | ELEDLQVEQAELGLEAGGLQPSALEMILQ (SEQ ID NO. 27) |
| Q62543 (western wild mouse) | GGPGAGDLQTLALEVAQQ (SEQ ID NO. 28) |
| Q62542 (western wild mouse) | GSPGDLQTLALEVARQ (SEQ ID NO. 29) |
| Ins_Anap1 (domestic duck) | DVEQPLVNGPLKGEVGELPPQHEEYQXX (SEQ ID NO. 30) |
| Ins_Chick (chicken) | DVEQPLYSSPLKGEAGYLPPQQEEYEKV (SEQ ID NO. 31) |

Figure 5

Teased fiber assessment of nodal and axonal morphometric changes in healthy controls and diabetic rats receiving C-peptide treatment for 8 weeks with different administration regimens

| Frequency of fibers (%) showing | Non-Diabetic Controls | Diabetic untreated | C-peptide Treatment | | |
|---|---|---|---|---|---|
| | | | Once Daily | Continuous infusion | Three times daily |
| Paranodal swelling | 1.03 ± 0.16 | 7.60 ± 0.37 | 2.49 ± 0.15* | 1.53 ± 0.18 | 1.78 ± 0.16 |
| Paranodal demyelination | 0.09 ± 0.08 | 2.22 ± 0.12 | 1.01 ± 0.13* | 0.24 ± 0.10 | 0.45 ± 0.16 |
| Excessive wrinkling | 0.68 ± 0.07 | 3.63 ± 0.35 | 0.57 ± 0.14* | 0.55 ± 0.11 | 0.58 ± 0.10 |
| Axonal degeneration | 0.30 ± 0.17 | 1.84 ± 0.39 | 0.43 ± 0.16* | 0.30 ± 0.10 | 0.38 ± 0.19 |

Mean values ± SE are given
* Significantly lower than the corresponding value for untreated diabetic animals, $P < 0.01$

THERAPEUTIC APPLICATIONS FOR C-PEPTIDE

RELATED APPLICATIONS

This application is a U.S. National Phase under 35 USC 371 of International Application No.: PCT/GB2004/004341, filed Oct. 13, 2004, designating the U.S. and published in English on May 6, 2005 as WO 2005/039627, which claims the benefit of British application No.: GB 0323979.5, filed Oct. 13, 2003.

FIELD OF THE INVENTION

The present invention relates to administration of C-peptide in a once daily dose, for use in the treatment of diabetes and diabetic complications.

BACKGROUND OF THE INVENTION

Insulin-dependent diabetes mellitus (IDDM), generally synonymous with type 1 diabetes, is the classical, life-threatening form of diabetes, the treatment of which was revolutionized by the discovery of insulin in 1922. The prevalence of type 1 diabetes is unfortunately widespread throughout much of the world and hence type 1 diabetes represents a serious condition with a significant drain on health resources.

The etiology of type 1 diabetes is multifactorial and not yet entirely clear. However it is characterised by a partial or complete autoimmune destruction of the pancreatic beta cells. In the acute phase of type 1 diabetes insulin deficiency is thus the dominating pathophysiological feature.

After starting insulin treatment many patients enjoy good blood glucose control with only small doses of insulin. There is an early phase, the "honeymoon period", which may last a few months to a year and which probably reflects a partial recovery of beta cell function. This is, however, a temporary stage and ultimately, the progressive destruction of the beta cells leads to complete cessation of insulin secretion and increasing requirements for exogenous insulin.

While the short term effects of hypoinsulinemia in the acute phase of type 1 diabetes can be well controlled by insulin administration, the long term natural history of type 1 diabetes is darkened by the appearance in many patients of potentially serious complications known as late, or late onset complications. These include the specifically diabetic problems of nephropathy, retinopathy and neuropathy. These conditions are often referred to as microvascular complications even though microvascular alterations are not the only cause. Atherosclerotic disease of the large arteries, particularly the coronary arteries and the arteries of the lower extremities, may also occur.

Nephropathy develops in approximately 35% of, type 1 diabetes patients, particularly in male patients and in those with onset of the disease before the age of 15 years. Diabetic nephropathy is characterized by persistent albuminuria secondary to glomerular capillary damage, a progressive reduction of the glomerular filtration rate and eventually, end stage renal failure requiring dialysis treatment or kidney transplantation.

The prevalence of diabetic retinopathy is highest among young-onset type 1 diabetes patients and it increases with the duration of the disease. Proliferative retinopathy is generally present in about 25% of the patients after 15 years duration and in over 50% after 20 years. The earliest lesion of diabetic retinopathy is a thickening of the capillary basement membrane, followed by capillary dilation and leakage and formation of microaneurysms. Subsequently, occlusion of retinal vessels occurs resulting in hypoperfusion of parts of the retina, oedema, bleeding and formation of new vessels as well as progressive loss of vision.

The diabetes-induced nerve disorder is most often a distal symmetric primarily sensory neuropathy affecting 30-50% of type 1 patients. It is often associated with autonomic dysfunction. Sensory neuropathy may cause loss of sensation, appearance of paraaestesia or numbness or, alternatively, result in unpleasant sensations, sometimes pain, in the legs, feet or hands. The morphological changes of diabetic peripheral neuropathy include distal axonal loss with a reduction of the number of large (myelinated) and small fibers, focal demyelinisation and regenerating activity. The function abnormalities include slowing of nerve conduction velocities, reduction of nerve signal amplitudes and rises in sensory modality thresholds. Autonomic neuropathy afflicts approximately 50% of the patients with type 1 diabetes of more than 15 years duration. It may evolve through defects in thermoregulation, impotence and bladder dysfunction followed by cardiovascular reflex abnormalities. Late manifestations may include generalized sweating disorders, postural hypotension, gastrointestinal problems and reduced awareness of hypoglycemia. The latter symptom has grave clinical implications.

A number of theories have been advanced with regard to possible mechanism(s) involved in the pathogenesis of the different diabetic complications but this has not yet been fully elucidated. Metabolic factors may be of importance and it has been shown that good metabolic control is accompanied by significantly reduced incidence of complications of all types. Nevertheless, after 7-10 years of good metabolic control, as many as 15-25% of the patients show signs of beginning nephropathy, 10-25% have symptoms of retinopathy and 15-20% show delayed nerve conduction velocity indicating neuropathy. With longer duration of the disease the incidence of complications increases further. There is thus a significant clinical need for the control and management of these diabetic complications.

In addition to IDDM (type I diabetes), other types of diabetes are known. Diabetes mellitus is the chronic syndrome of impaired carbohydrate, protein and fat metabolism owing to insufficient secretion of insulin or to target tissue insulin resistance. It occurs in two major forms, type I as discussed above, and type II, non-insulin dependent diabetes mellitus, which differs in etiology, pathology, genetics, age of onset and treatment. Generally, there is no requirement for exogenous insulin in the treatment of type II diabetes. Other forms of diabetes, beyond diabetes mellitus, also exist. Whilst complications, e.g. micro angiopathic complications affecting the retinas and kidneys are seen with higher incidence in type I diabetes, it is not precluded that complications, including those which occur in type I, may occur also with type II diabetes, and other forms of diabetes.

Proinsulin C-peptide is a part of the proinsulin molecule which, in turn, is a precursor to insulin formed in the beta cells of the pancreas. For a long time it was believed that C-peptide (known variously as C-peptide or proinsulin C-peptide) had no role other than as a structural component of proinsulin, facilitating correct folding of the insulin part. However, it has in more recent years been recognised that C-peptide has a physiological role as a hormone in its own right (Wahren et al., (2000), Am. J. Physiol. Endocrinol. Metab, 278, E759-E768). In diabetic patients, it alleviates renal dysfunction, improves blood flow in several tissues, ameliorates nerve functional impairments and is believed to delay or prevent the onset of late complications (Wahren et al., (2000) supra; Johansson J et al. Biochem Biophysical Research Comm.

2002; 295:1035-1040; Wahren et al. in International Textbook of Diabetes, 3rd Edition, editors DeFronzo, Ferrannini, Keen and Zimmet, 2004, Wiley, London). Indeed, C-peptide has been proposed for use in the treatment of diabetes in EP 132769 and in SE460334 for use in combination with insulin in the treatment of diabetes and prevention of diabetic complications.

C-peptide is known to have a relatively short half-life. In humans the half-life is approximately 30 minutes and a dose of C-peptide injected into a rat would be expected to have disappeared entirely from circulation within 2-3 hours. Due to the short half-life of C-peptide, in all prior art disclosures several daily doses (typically 3 or 4) or a continuously administered dose are used to treat diabetes or diabetic complications. For example, Sima et al. (Diabetologia, 44, 889-897, 2001) administered C-peptide in a continuous dose by osmopump to diabetic rats. In one known case Ido et al. (Science, 277, 563-566, 1997) administered C-peptide (at 130 nmol per kilogram of bodyweight) twice daily to rats with streptozotocin-induced diabetes. However, in this study human C-peptide was given to rats in a dose approximately five fold per kg body weight higher than otherwise used. Human C-peptide can be expected to be catabolized more slowly in the rat than the homologous C-peptide, which together with the high dosage may account for the observed effect in this study.

Similarly, insulin, which is derived from the same prohormone (proinsulin) as C-peptide requires administration 3-5 times daily.

SUMMARY OF THE INVENTION

The inventors of the present application have now surprisingly found that C-peptide given in a once daily dose can be used to treat diabetes, and particularly type I diabetes, and diabetic complications effectively. This is particularly surprising since a once daily administration of C-peptide would be expected to leave an animal without detectable C-peptide levels for at least 18-20 hours per day (approximately 75-80% of the time). Thus a new mechanism of action for C-peptide is suggested, as it is not believed that the C-peptide remains in the plasma at levels which are sufficient to explain the beneficial effects. This finding offers significant practical advantages to doctor and patient alike in the treatment of diabetes and diabetic complications.

Thus, in one aspect the present invention provides a use of C-peptide in the manufacture of a medicament for administration to a patient as a once daily dose for the treatment of diabetes and/or diabetic complications.

As defined and described further below the term "C-peptide" includes functionally equivalent fragments, derivatives or variants of C-peptide, e.g. of a native or naturally occurring or wild-type C-peptide sequence.

Thus alternatively viewed, this aspect of the invention can be seen to provide use of C-peptide or a functionally equivalent fragment, derivative or variant thereof in the manufacture of a medicament for administration to a patient as a once daily dose for the treatment of diabetes and/or diabetic complications.

"Diabetes" includes any form of diabetes. This may be defined generally as any disorder characterised by excessive urine excretion (polyuria). Thus, both type I and type II diabetes mellitus are covered, as well as any disorder falling under the general heading of diabetes. Particularly, the invention concerns types I and II diabetes, and/or the complications thereof, especially type I diabetes and/or the complications thereof.

'Diabetic complications' refer to the complications of any form of diabetes, but particularly of type I diabetes. These may include any complication known or found to be associated with diabetes, particularly type I diabetes. Specifically, the complications of diabetic nephropathy, retinopathy and neuropathy are included. Such complications are believed to share, as a major pathogenic factor, a dysfunction of the small blood vessels in the tissues concerned (specifically in the case of nephropathy, retinopathy and neuropathy, in the kidneys, the eyes and the nervous system). Thus the diabetic complications of particular concern in the present invention may be viewed as microvascular complications (i.e. complications involving or associated with small blood vessels).

Many of the complications are linked to a reduction in $Na^+K^+ATPase$ activity and therefore in a further embodiment, the invention provides the use of C-peptide in the manufacture of a medicament for administration to a patient as a once daily dose for use in stimulating $Na^+K^+ATPase$ in a patient and/or for treating or preventing conditions associated with a sub-normal $Na^+K^+ATPase$ activity.

Alternatively viewed, the invention provides the use of C-peptide in the manufacture of a medicament for the treatment of diabetes and/or diabetic complications, characterised in that the medicament is for once daily administration to a patient.

Also, the invention provides C-peptide for use as a once daily dose in therapy, in particular in the treatment of diabetes and/or diabetic complications.

The present invention also provides the use of C-peptide in the manufacture of a medicament for the treatment of diabetes and/or diabetic complications by administration once a day. Preferably the invention provides the use of C-peptide in the manufacture of a medicament in the form of an aqueous solution for the treatment of diabetes and/or diabetic complications by administration (of said medicament) once a day.

In all the uses mentioned above, the C-peptide may be C-peptide or a functionally equivalent fragment, derivative or variant thereof.

Reference to a 'once daily dose' or 'once daily administration' means, of course, not only that the medicament itself is only given once per day but that the patient receives no other C-peptide treatment. Such instructions may be made clear by the prescribing physician and/or in literature accompanying the packaged medication. The medicament may be adapted for once daily administration. This does not imply the presence of substances which act as release rate controlling agents, indeed the most preferred formulation of the invention is an uncompromised aqueous solution. However, the fact that a single, rather than multiple, dose is given may be reflected in the amount of active agent administered in the single dose, which may be more than would typically be administered in a dose prepared for thrice daily administration for example. Thus, different amounts may be given in a single dose, which may be greater than the amounts which would be administered in a dose intended for administration more than once. Thus, a single dose may have a higher concentration of active agent or the dose may be administered in a greater amount, e.g. a greater volume. Specific doses are described below. A once daily dose does not cover a continuous administration and is distinct therefrom. A once daily dose hence is directed to only one administration per day of the C-peptide treatment whereas a continuous administration would be constantly administering C-peptide treatment, or administering it over a prolonged period of time.

The term "C-peptide" as used herein includes all forms of C-peptide (also known as proinsulin C-peptide), including native or synthetic peptides. Such C-peptides may be the human peptide, or may be from other animal species and genera, preferably mammals. "C-peptide" or "pro-insulin C-peptide" as used herein covers C-peptide isolated from any species. Preferably, "C-peptide" refers to human C-peptide having the amino acid sequence EAEDLQVGQVELGGGP-GAGSLQPLALEGSLQ (SEQ ID NO. 1). Thus, variants of human C-peptide are included, which may be native variants, or synthetically or artificially derived. C-peptides from a number of different species have been sequenced and are known in the art. It would thus be a routine matter to select a variant being a C-peptide from a species or genus other than human. Several such variants of C-peptide (i.e. representative C-peptides from other species) are shown in FIG. 1 (see SEQ ID NOS. 1 and 9-31). Thus variants and modifications of native human C-peptide are included as long as they retain C-peptide activity. The C-peptides may be in their native form, i.e. as different variants as they appear in nature in different species or due to geographical variation etc., which may be viewed as functionally equivalent variants of human C-peptide or they may be functionally equivalent derivatives thereof, which may differ in their amino acid sequence, for example by truncation (e.g. from the N- or C-terminus or both) or other amino acid deletions, additions, insertions or substitutions. It is known in the art to modify the sequences of proteins or peptides, whilst retaining their useful activity and this may be achieved using techniques which are standard in the art and widely described in the literature e.g. random or site-directed mutagenesis, cleavage and ligation of nucleic acids etc.

Any such modifications, or combinations thereof, may be made, as long as activity is retained. The C-terminal end of the molecule is believed to be important for activity. Preferably, therefore, the C-terminal end of the C-peptide should be preserved in any such C-peptide variants or derivatives, more preferably the terminal pentapeptide of C-peptide should be preserved. Modifications to the mid-part of the C-peptide sequence (e.g. to residues 13 to 25 of human C-peptide) allow the production of functional derivatives or variants of C-peptide and are hence covered.

Thus C-peptides which may be used according to the invention may have amino acid sequences which are substantially homologous, or substantially similar to the native C-peptide amino acid sequences, for example to the human C-peptide sequence of SEQ ID NO. 1 or any of the other native C-peptide sequences shown in FIG. 1. Such substantially homologous sequences may include those having at least 30% (or more preferably at least 40, 50, 60, 70, 75, 80, 85, 90, 95, 98 or 99%) similarity to any one of SEQ ID Nos. 1 or 9 to 31 as shown in FIG. 1, preferably to the native human sequence of SEQ ID No. 1. Alternatively, the C-peptide may have an amino acid sequence having at least 30% (or more preferably at least 40, 50, 60, 70, 75, 80, 85, 90, 95, 98 or 99%) identity with the amino acid sequence of any one of SEQ ID Nos. 1 or 9 to 31 as shown in FIG. 1, preferably with the native human sequence of SEQ ID No. 1. Although any amino acid of C-peptide may be altered as described above, it is preferred that one or more of the glutamic acid residues at positions 3, 11 and 27 of human C-peptide (SEQ ID NO. 1) or corresponding or equivalent positions in C-peptide of other species, are conserved. Preferably all of the glutamic acid residues at positions 3, 11 and 27 (or corresponding Glu residues) of SEQ ID NO. 1 are conserved.

Amino acid sequence identity or similarity may be determined using the BestFit program of the Genetics Computer Group (GCG) Version 10 Software package from the University of Wisconsin. The program uses the local homology algorithm of Smith and Waterman with the default values: Gap creation penalty=8, Gap extension penalty=2, Average match=2.912, Average mismatch=2.003. Thus, functionally equivalent derivatives or variants of native C-peptide sequences may readily be prepared according to techniques well known in the art, and include peptide sequences having a functional, e.g. a biological, activity of a native C-peptide.

Fragments of native or synthetic C-peptide sequences may also have the desirable functional properties of the peptide from which they derive and are hence also included.

The term "fragment" as used herein thus includes fragments of a C-peptide provided that the fragment retains the biological or therapeutically beneficial activity of the whole molecule. Preferred fragments comprise residues 15-31 of native C-peptide, more especially residues 20-31. Peptides comprising the pentapeptide EGSLQ (SEQ ID NO. 2) (residues 27-31 of native human C-peptide) are also preferred. The fragment may thus vary in size from e.g. 4 to 30 amino acids or 5 to 20 residues.

Suitable fragments are disclosed in WO 98/13384 the contents of which are incorporated herein by reference. Representative fragments include ELGGGPGAG (SEQ ID NO. 3), EGSLQ (SEQ ID NO. 2), ELGG (SEQ ID NO. 4), ELGGGP (SEQ ID NO. 5), GGPGA (SEQ ID NO. 6) or GSLQ (SEQ ID NO. 7). The fragment may also include an N-terminal fragment of C-peptide, typically having the sequence EAEDLQVGAVEL (SEQ ID NO. 8), or a fragment thereof which comprises 2 acidic amino acid residues, capable of adopting a conformation where said two acidic amino acid residues are spatially separated by a distance of 9-14 Å between the α-carbons thereof.

Also included are fragments having N and/or C-terminal extensions or flanking sequences. The length of such extended peptides may vary, but typically are not more than 50, 30, 25 or 20 amino acids in length. In such a case it will be appreciated that the extension or flanking sequence will be a sequence of amino acids which is not native to a naturally-occurring or native C-peptide, and in particular a C-peptide from which the fragment is derived. Such a N- and/or C-terminal extension or flanking sequence may comprise e.g. from 1 to 10, e.g. 1 to 6, 1-5, 1-4 or 1-3 amino acids.

Nevertheless, C-peptide itself, especially human C-peptide is particularly preferred. Also peptides very closely based on SEQ ID No. 1 are particularly preferred, e.g. those incorporating 1-10, 1-6, 1-4 or 1-3 additional or deleted amino acids or amino acid substitutions, such substitutions preferably being conservative.

The term "derivative" as used herein thus refers to C-peptide sequences or fragments thereof, which have modifications as compared to the native sequence.

Such modifications may be one or more amino acid deletions, additions, insertions and/or substitutions. These may be contiguous or non-contiguous. Representative such variants may include those having 1 to 6, or more preferably 1 to 4, 1 to 3 or 1 or 2 amino acid substitutions as compared to SEQ ID No. 1. The substituted amino acid may be any amino acid, particularly one of the well known 20 conventional amino acids (Ala (A); Cys (C); Asp (D); Glu (E); Phe (F); Gly (G); His (H); Ile (I); Lys (K); Leu (L); Met (M); Asn (N); Pro (P); Gln (Q); Arg (R); Ser (S); Thr (T); Val (V); Trp (W); and Tyr (Y)).

Chemical modification of the peptide structure is not precluded e.g. by glycosylation as long as the structure of the derivative remains essentially peptide in nature. As mentioned above, modification of an amino acid sequence may be by amino acid substitution, for example an amino acid may be replaced by another which preserves the physicochemical character of the peptide (e.g. A may be replaced by G or vice versa, V by A, L or G; E by D or vice versa; and Q by N). Generally, the substituting amino acid has similar properties e.g. hydrophobicity, hydrophilicity, electronegativity, bulky side chains etc. to the amino acid being replaced. Isomers of the 'native' L-amino acid, e.g. D-amino acids may be incorporated.

Additional variants may include amino and/or carboxyl terminal fusions as well as intrasequence insertions of single or multiple amino acids. Longer peptides may comprise multiple copies of one or more of the peptide sequences. C and N-terminal protecting groups may be included.

Insertional amino acid sequence variants are those in which one or more amino acid residues are introduced at a site in the protein. Deletional variants are characterised by the removal of one or more amino acids from the sequence.

"Variants" may include, for example, different allelic variants as they appear in nature, e.g. in other species or due to geographical variation etc.

All such variants, derivatives or fragments of C-peptide are included, and are subsumed under the term "C-peptide".

The variants, derivatives and fragments are functionally equivalent in that they have C-peptide activity. More particularly, they exhibit at least 40%, preferably at least 60%, more preferably at least 80% of the activity of proinsulin C-peptide, particularly human C-peptide. Thus they are capable of functioning as proinsulin C-peptide i.e. can substitute for C-peptide itself.

Such activity means any activity exhibited by a native C-peptide, whether a physiological response exhibited in an in vivo or in vitro test system, or any biological activity or reaction mediated by a native C-peptide, for example in an enzyme assay or in binding to test tissues or membranes.

Thus, it is known that C-peptide increases the intracellular concentration of calcium. An assay for C-peptide activity can thus be by assaying for changes in intracellular calcium concentrations upon addition or administration of the peptide (e.g. fragment or derivative) in question. Such an assay is described in for example Ohtomo et al., (1996), Diabetologia, 39, 199-205; Kunt et al., Diabetes, 47, A30; Shafqat et al., 2002, Cell Mol. Life Sci., 59, 1185-1189 and in Example 1 below.

Further, C-peptide has been found to induce phosphorylation of the MAP-kinases ERK 1 and 2 of a mouse embryonic fibroblast cell line (Swiss 3T3), and measurement of such phosphorylation and MAPK activation may be used to assess, or assay for C-peptide activity, as described for example by Kitamura et al., 2001 Biochem J., 355, 123-129 and in Example 2.

C-peptide also has a well known effect in stimulating $Na^+K^+$ATPase activity and this also may form the basis of an assay for C-peptide activity, for example as described in WO 98/13384 or in Ohtomo et al., (1996), supra or Ohtomo et al., (1998), Diabetologia, 41, 287-291.

An assay for C-peptide activity based on endothelial nitric oxide synthase (eNOS) activity is also described in Kunt et al., supra, using bovine aortic cells and a reporter cell assay.

Binding to particular cells may also be used to assess or assay for C-peptide activity, for example to cell membranes from human renal tubular cells, skin fibroblasts and saphenous vein endothelial cells using fluorescence correlation spectroscopy, as described for example in Rigler et al., 1999, PNAS USA 96, 13318-13323; Henriksson et al., 2000, Cell Mol. Life Sci 57, 337-342 and Pramanik et al., 2001, BBRC 284, 94-98. Finally, affinity tests based on measurements of protein binding may be used as activity tests of C-peptide.

The "patient" can be any animal but preferably is a human.

Administration of the single daily dose may be by any suitable method known in the medicinal arts, including oral, parenteral, topical, subcutaneous administration or by inhalation. Preferably administration is by subcutaneous administration. The single dose may be administered at any time during the day. For humans, the dosage used may range from 0.5-30 nmol/kg of bodyweight/24 hours of C-peptide, for example 3-30 or 0.5 to 20 or 0.5 to 15 or 0.5 to 10 nmol/kg of bodyweight/24 hours. Preferably the dose used is 1-20. 1-15, 1-10 or 1-5 nmol/kg of bodyweight/24 hours. The dose may be 1, 2, 3, 4, 5, 6, 7, 8, 9, 10, 11, 12, 13, 14, 15, 16, 17, 18, 19 or 20 nmol/kg of bodyweight/24 hours. Thus a single dose as administered will vary depending on the weight of the patient but may typically be in the region of 100-2000 nmol, 100-1800, 100-1500, 100-1200, 100-1000 or 100-800 nmol. Other ranges include 200-1800, 200-1200 or 1200 to 1800 nmol. Representative single doses thus include about 1500, 1200, 1000, 900, 800, 700, 600, 500, 450, 400, 300, 200 or 150 nmol.

The dose may or may not be in solution. If the dose is administered in solution, it will be appreciated that the volume of the dose may vary, but will typically be 10 µl-1 ml. Preferably the dose will be given in a volume of 900 µl, 800 µl, 700 µl, 600 µl, 500 µl, 400 µl, 300 µl, 200 µl, 100 µl, 50 µl or 20 µl.

Aqueous solutions of C-peptide are preferred.

The C-peptide dose in solution can also comprise a preservative and/or a buffer. For example, the preservative m-cresol can be used. Typical concentrations of preservatives include 0.5 mg/ml, 1 mg/ml, 2 mg/ml, 3 mg/ml, 4 mg/ml or 5 mg/ml. Thus, a range of concentration of preservative may include 0.2 to 10 mg/ml, particularly 0.5 to 6, or 0.5 to 5 mg/ml. Examples of buffers that can be used include sodium phosphate buffer (pH 7.3) or sodium bicarbonate buffer (pH 7.3). It will be appreciated that the C-peptide dose may comprise of one or more of a native or intact C-peptide, fragments, derivatives or other functionally equivalent variants of C-peptide. Hence, the single dose may comprise human C-peptide and the C-terminal C-peptide fragment EGSLQ (SEQ ID NO. 2) and/or an N-terminal C-peptide fragment, e.g. SEQ ID NO. 8. Further, the dose may if desired only contain a fragment of C-peptide, for example EGSLQ. Thus, the term "C-peptide" may encompass a single C-peptide entity or a mixture of different "C-peptides".

In a further embodiment, the present invention provides the use of a pharmaceutical composition comprising C-peptide in the manufacture of a medicament for administration to a patient as a once daily dose for the treatment of diabetes and/or diabetic complications.

Also provided is a pharmaceutical composition comprising C-peptide together with at least one pharmaceutically acceptable carrier or excipient for administration (or when administered) to a patient as a once daily dose for the treatment of diabetes and/or diabetic complications.

Pharmaceutical compositions for use in the present invention may be formulated according to techniques and procedures well known in the art and widely discussed in the literature and may comprise any of the known carriers, diluents or excipients. The compositions may be in the form of (sterile) aqueous solutions and/or suspensions of the pharmaceutically active ingredients, aerosols, ointments and the like. Formulations which are aqueous solutions are most preferred. Such formulations typically contain the peptide itself, water and one or more buffers which act as stabilisers (e.g. phosphate containing buffers) and optionally one or more preservatives. Such formulations containing, e.g. 100-2000 nmol, 100-1500, 100-1000, or 200-1800 nmol or 1200 to 1800 nmol or any of the ranges mentioned above e.g. about 1500, 1400, 1300, 1200, 1100, 1000, 900, 800, 700, 600, 500, 450, 400, 300, 200 or 150 nmol of the peptide constitute a further aspect of the invention.

Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol and the like.

Compositions of the invention suitable for oral administration may for example comprise peptides in sterile purified stock powder form preferably covered by an envelope or envelopes (enterocapsules) protecting from degradation of the peptides in the stomach and thereby enabling absorption of these substances from the gingiva or in the small intestines.

The total amount of active ingredient in the composition may vary from 99.99 to 0.01 percent of weight.

As discussed above, the C-peptide dose and pharmaceutical compositions containing this dose can be used in the manufacture of a medicament to treat diabetes and diabetic complications. Such diabetic complications include retinopathy, nephropathy and neuropathy. The administration of the single C-peptide dose can hence be used to improve nerve cell structure (paranodal swelling, paranodal demyelinsation, intercalated internodes, Wallerian degeneration, regeneration, sequential demyelinisation and excessive wrinkling). An improvement in $Na^+K^+ATPase$ activity may also be observed. 'Treatment' includes a measurable improvement in one or more of these complications or in the parameters which define diabetes, e.g. type I diabetes e.g. reduction in urinary albumin excretion, reduction or maintenance of plasma creatinine concentration, maintenance or increase in glomerular filtration rate, or improvement in retinal-vitreous body leakage, aneurysm formation or retinal bleeding. The once-daily therapeutic regimen described herein may, optionally in combination with conventional insulin therapy, be useful in preventing or substantially retarding the development of the late diabetic complications discussed above. Thus there may be a prophylactic element to the 'treatments' discussed above.

In a further aspect the invention provides a therapeutic regimen for the treatment of diabetes and/or the complications thereof wherein C-peptide is administered once daily to a patient.

In another embodiment, the invention provides a method of treating diabetes and/or diabetic complications in a patient comprising administering C-peptide in a once daily dose.

Methods of treatment corresponding to the various additional uses discussed above are further aspects of the invention.

The method also covers a method of treatment comprising administering one dose of a pharmaceutical composition of the invention.

BRIEF DESCRIPTION OF THE DRAWINGS

The invention will now be described in more detail in the following non-limiting Examples and with reference to the drawings in which:

FIG. 1 is an alignment showing all reported C-peptide amino acid sequences;

FIG. 5 is a table showing teased fiber assessment of nodal and axonal morphometric changes in healthy controls and diabetic rats receiving C-peptide treatment for 8 weeks with different administration regimens.

DETAILED DESCRIPTION OF THE PREFERRED EMBODIMENT

EXAMPLES

Example 1

Figure 2:
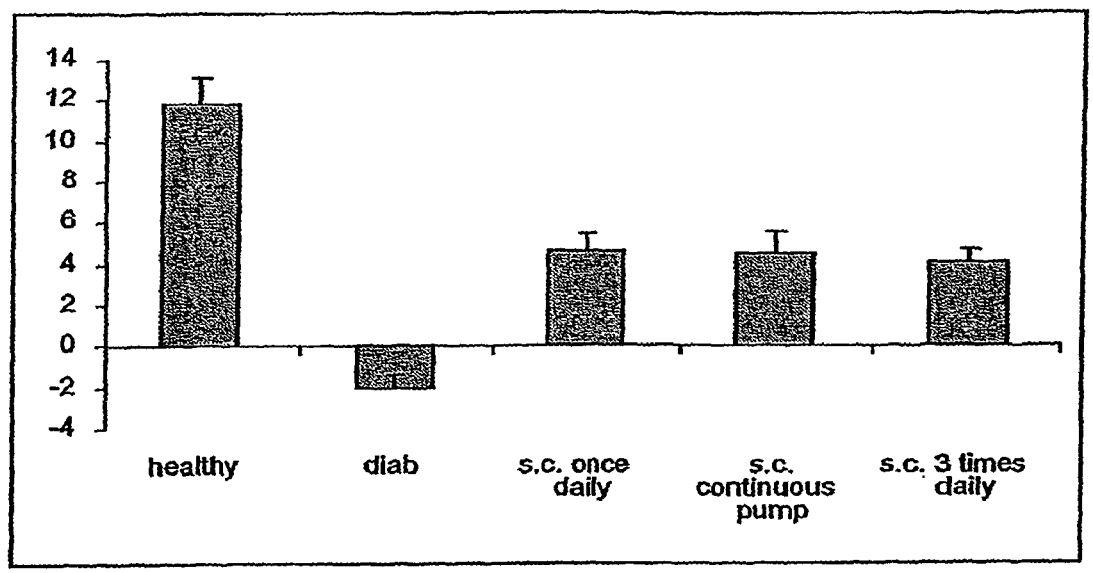
FIG. 2 is a graph showing changes in motor nerve conduction velocity (MNCV) expressed in m/s in healthy control and diabetic animals receiving C-peptide treatment for 8 weeks with different dosing regimens; diab=diabetic, s.c.=subcutaneous.

Further technical details can be found in Sima et al., Diabetologia (2001) 44: 889-897.

Prediabetic male BB/Wor rats were used. Ten rats were used in each group, where the animals were closely age-matched. They were maintained in metabolic cages with free access to water and rat chow. Bodyweight, urine volume and glucosuria were monitored daily to ascertain onset of diabetes. Immediately after the onset of diabetes, administration of C-peptides was commenced in either a single dose/24 hours, three doses/24 hours or as a continuous infusion by osmopump.

The single dose given was 75 nmol/kg and the three doses given were each 25 nmol/kg. The continuous infusion gave a dose of 75 nmol/kg over a 24 hour period.

Synthetic rat C-peptide II with a purity of more than 98% by HPLC was used (Genosys, Cambridge, UK) dissolved in saline (12 mg/ml). Control rats were given a dose of saline instead of C-peptide.

The nerve conduction velocity in motor and sensory nerves and $Na^+K^+ATPase$ levels in the rats were measured. Baseline nerve conduction velocity was measured within 24 hours of onset of diabetes. Measurements were taken in the sciatic-tibial nerves under temperature-controlled conditions (35° C.-37° C.) as in Sima et al. J. Clin. Invest. (1996) 97: 1900-1907.

To measure $Na^+K^+ATPase$ activity and investigate nerve cell morphology, animals were anaesthetized with Na-pentobarbital (50 mg/kg bodyweight i.p.) and both sciatic nerves were dissected, weighed and snap frozen in liquid nitrogen for measurements of nerve glucose, sorbitol, fructose and $Na^+K^+ATPase$ activity. The right sural nerve was fixed in 7.5% glutar aldehyde in 0.1 mol/l cacodylate buffer at pH 7.40 and post fixed in 1% osmium tetroxide (pH 7.40). The distal sural nerve was used for teased fibre preparations.

Insulin and C-peptide concentrations. Serum insulin and C-peptide concentrations were examined using commercially available RIA kits (Linco Research, St. Charles, Mo., USA).

Biochemical analyses. For nerve glucose, sorbitol and fructose, sciatic nerve samples were homogenized in 2 ml of 5% TCA. Aldonitrile derivatives were formed by adding 0.3 ml hydroxylamine in pyridine-methanol 4:1 (vol:vol). Samples were sonicated for 1 mm and 1 ml of acetic anhydride and 2 ml of 1,2 dichlorothane were added and samples were washed in 1.0 N HCl. Samples were reconstituted in 2-butanane and analysed by gas-liquid chromatography.

For Na$^+$/K$^+$-ATPase activity, nerve samples were homogenized in 2 ml of 0.2 mol/l sucrose and 0.02 mol/l TRIS-HCl at pH 7.5. Between 10 and 20 µl of the homogenate was assayed enzymatically for total ATPase in 1 ml of 100 mmol/l NaCl, 10 mmol/l KCl, 2.5 mmol/l MgCl$_2$, 1 mmol/l TRIS ATP, 1 mmol/l phosphoenolpyruvate, 30 mmol/l imidazole HQ buffer (pH 7.30), 0.15 mmol/l NADH, 50 pg lactate dehydrogenase and 30 µg pyruvate kinase. To measure ouabain-inhibited ATPase, 20 µl of 25 mmol/l of ouabain was added. Na$^+$/K$^+$-ATPase activity was defined as the difference before and after ouabain and was expressed as µmol ADP formed per gram of wet weight per hour.

Morphometric analysis. Semithin (0.5 µm) cross-sections of sural nerves were used for morphometric analysis. The following measurements of myelinated fibres were obtained: total number, axonal and myelin size (µm$^2$), fibre density (n/mm$^2$), coefficient of variance (CV) of fibre densities between image frames, fibre occupancy (% of endoneurial area), and axon to myelin ratio.

Teased fibre examinations. A mean of 168±4 myelinated fibres were teased from each sural nerve and scored for specific changes. The temporal sequence and increasing severity are represented by normality, paranodal swelling, paranodal demyelination, excessive myelin wrinkling, intercalated inter-nodes, segmental demyelination, Wallerian degeneration, and regeneration. Changes were expressed as percentages of total fibres.

Statistical analysis. The results are presented as means±SE and the significance of differences was calculated by analysis of variance (ANOVA). Group differences were assessed by post hoc analysis using the Student-Newman-Keul test. Tissue samples for biochemical, morphometric and teased fiber analyses were coded to mask animal identity. A p value of less than 0.05 was considered statistically significant.

RESULTS

Figure 3:
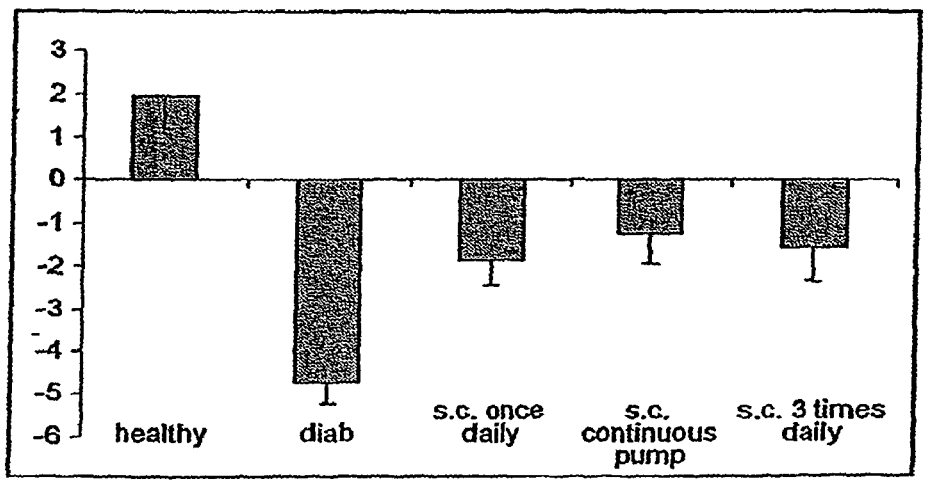
FIG. 3 is a graph showing changes in sensory nerve conduction velocity (SNCV) expressed in m/s in healthy control and diabetic animals receiving C-peptide treatment for 8 weeks with different dosing regimens.
Figure 4:
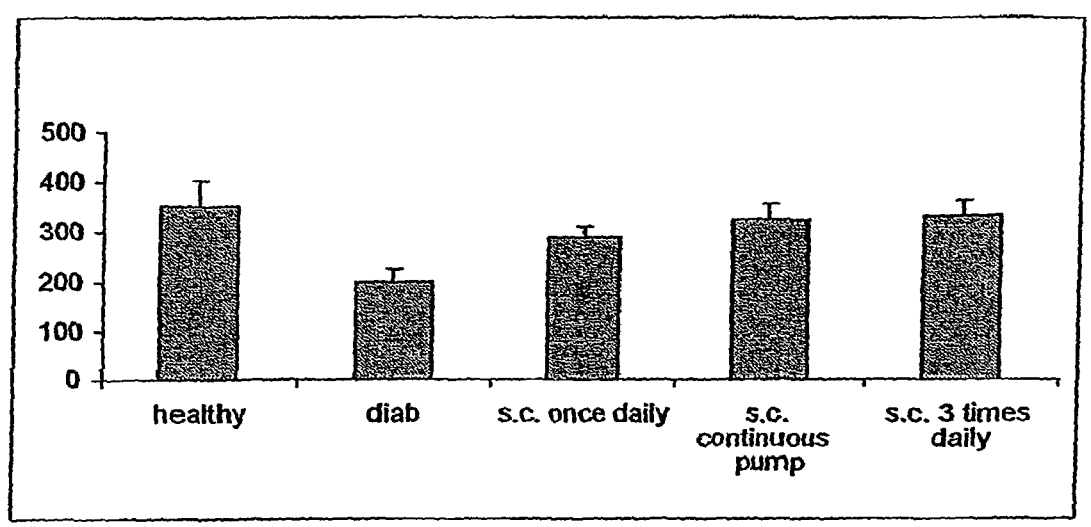
FIG. 4 is a graph showing $Na^+K^+ATPase$ activity in the sciatic nerve (μmol ADP/mg/h) in healthy control and diabetic rats receiving C-peptide treatment for 8 weeks with different dosing regimens.

The results can be seen in FIGS. 2 to 5. The results show that nerve conduction velocity and Na$^+$K$^+$ATPase activity is clearly and sufficiently improved in rats given a once daily dose of C-peptide and that the once daily dose is as effective as three daily dose or a continuous infusion.

The morphometric data also show improved morphology of cells in rats given a once daily dose of C-peptide compared to diabetic rats.

---

What is claimed is:

1. A method of treating diabetes and/or microvascular diabetic complications comprising administering C-peptide or a pharmaceutical composition comprising C-peptide to a patient once daily wherein said once daily administration does not include a continuous administration or the presence of release rate-controlling agents, wherein said administration is by subcutaneous administration, and wherein said pharmaceutical composition contains 100 to 1800 nmol of C-peptide.

2. The method according to claim 1, wherein said C-peptide is human C-peptide.

3. The method according to claim 1, wherein said C-peptide is a fragment EGSLQ (SEQ ID NO: 2).

4. The method according to claim 1, wherein said patient is a human.

5. The method according to claim 1, wherein said C-peptide is in an aqueous solution.

6. The method according to claim 1, wherein said complications are diabetic nephropathy, retinopathy or neuropathy.

7. The method according to claim 6, wherein said complications are diabetic neuropathy.

* * * * *

SEQUENCE LISTING

<160> NUMBER OF SEQ ID NOS: 31

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 5
<212> TYPE: PRT
<213> ORGANISM: Artificial Sequence
<220> FEATURE:
<223> OTHER INFORMATION: C-peptide fragment

<400> SEQUENCE: 2

Glu Gly Ser Leu Gln
1               5

<210> SEQ ID NO 3
<211> LENGTH: 9
<212> TYPE: PRT
<213> ORGANISM: Artificial Sequence
<220> FEATURE:
<223> OTHER INFORMATION: C-peptide fragment

<400> SEQUENCE: 3

Glu Leu Gly Gly Gly Pro Gly Ala Gly
1               5

<210> SEQ ID NO 4
<211> LENGTH: 4
<212> TYPE: PRT
<213> ORGANISM: Artificial Sequence
<220> FEATURE:
<223> OTHER INFORMATION: C-peptide fragment

```
<400> SEQUENCE: 4

Glu Leu Gly Gly
 1

<210> SEQ ID NO 5
<211> LENGTH: 6
<212> TYPE: PRT
<213> ORGANISM: Artificial Sequence
<220> FEATURE:
<223> OTHER INFORMATION: C-peptide fragment

<400> SEQUENCE: 5

Glu Leu Gly Gly Gly Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: C-peptide fragment

<400> SEQUENCE: 6

Gly Gly Pro Gly Ala
 1               5

<210> SEQ ID NO 7
<211> LENGTH: 4
<212> TYPE: PRT
<213> ORGANISM: Artificial Sequence
<220> FEATURE:
<223> OTHER INFORMATION: C-peptide fragment

<400> SEQUENCE: 7

Gly Ser Leu Gln
 1

<210> SEQ ID NO 8
<211> LENGTH: 12
<212> TYPE: PRT
<213> ORGANISM: Artificial Sequence
<220> FEATURE:
<223> OTHER INFORMATION: C-peptide fragment

<400> SEQUENCE: 8

Glu Ala Glu Asp Leu Gln Val Gly Ala Val Glu Leu
 1               5                  10

<210> SEQ ID NO 9
<211> LENGTH: 31
<212> TYPE: PRT
<213> ORGANISM: Pan troglodytes

<400> SEQUENCE: 9

Glu Ala Glu Asp Leu Gln Val Gly Gln Val Glu Leu Gly Gly Gly Pro
 1               5                  10                  15

Gly Ala Gly Ser Leu Gln Pro Leu Ala Leu Glu Gly Ser Leu Gln
             20                  25                  30

<210> SEQ ID NO 10
<211> LENGTH: 29
<212> TYPE: PRT
<213> ORGANISM: Aotus trivirgatus

<400> SEQUENCE: 10
```

```
Glu Ala Glu Asp Leu Gln Val Gly Gln Val Glu Leu Gly Gly Gly Ser
 1               5                  10                  15

Ile Thr Gly Ser Leu Pro Pro Leu Glu Gly Pro Met Gln
            20                  25
```

<210> SEQ ID NO 11
<211> LENGTH: 32
<212> TYPE: PRT
<213> ORGANISM: Macaca fascicularis

<400> SEQUENCE: 11

```
Glu Ala Glu Asp Pro Gln Val Gly Gln Val Glu Leu Cys Ser Gly Gly
 1               5                  10                  15

Pro Gly Ala Gly Ser Leu Gln Pro Leu Ala Leu Glu Gly Ser Leu Gln
            20                  25                  30
```

<210> SEQ ID NO 12
<211> LENGTH: 31
<212> TYPE: PRT
<213> ORGANISM: Cercopithecus aethiops

<400> SEQUENCE: 12

```
Glu Ala Glu Asp Pro Gln Val Gly Gln Val Glu Leu Gly Gly Gly Pro
 1               5                  10                  15

Gly Ala Gly Ser Leu Gln Pro Leu Ala Leu Glu Ser Ser Leu Gln
            20                  25                  30
```

<210> SEQ ID NO 13
<211> LENGTH: 29
<212> TYPE: PRT
<213> ORGANISM: Sus sp.

<400> SEQUENCE: 13

```
Glu Ala Glu Asn Pro Gln Ala Gly Ala Val Glu Leu Gly Gly Gly Leu
 1               5                  10                  15

Gly Gly Leu Gln Ala Leu Ala Leu Glu Gly Pro Pro Gln
            20                  25
```

<210> SEQ ID NO 14
<211> LENGTH: 26
<212> TYPE: PRT
<213> ORGANISM: Artificial Sequence
<220> FEATURE:
<223> OTHER INFORMATION: Boven C-peptide

<400> SEQUENCE: 14

```
Glu Val Glu Gly Pro Gln Val Gly Ala Leu Glu Leu Ala Gly Gly Pro
 1               5                  10                  15

Gly Ala Gly Gly Leu Glu Gly Pro Pro Gln
            20                  25
```

<210> SEQ ID NO 15
<211> LENGTH: 31
<212> TYPE: PRT
<213> ORGANISM: Equus sp.

<400> SEQUENCE: 15

```
Glu Ala Glu Asp Pro Gln Val Gly Glu Val Glu Leu Gly Gly Gly Pro
 1               5                  10                  15

Gly Leu Gly Gly Leu Gln Pro Leu Ala Leu Ala Gly Pro Gln Gln
            20                  25                  30
```

<210> SEQ ID NO 16

```
<211> LENGTH: 26
<212> TYPE: PRT
<213> ORGANISM: Ovis sp.

<400> SEQUENCE: 16

Glu Val Glu Gly Pro Gln Val Gly Ala Leu Glu Leu Ala Gly Gly Pro
1               5                   10                  15

Gly Ala Gly Gly Leu Glu Gly Pro Pro Gln
            20                  25

<210> SEQ ID NO 17
<211> LENGTH: 31
<212> TYPE: PRT
<213> ORGANISM: Canis sp.

<400> SEQUENCE: 17

Glu Val Glu Asp Leu Gln Val Arg Asp Val Glu Leu Ala Gly Ala Pro
1               5                   10                  15

Gly Glu Gly Gly Leu Gln Pro Leu Ala Leu Glu Gly Ala Leu Gln
            20                  25                  30

<210> SEQ ID NO 18
<211> LENGTH: 30
<212> TYPE: PRT
<213> ORGANISM: Oryctolagus cuniculus

<400> SEQUENCE: 18

Glu Val Glu Leu Gln Val Gly Gln Ala Glu Leu Gly Gly Gly Pro Gly
1               5                   10                  15

Ala Gly Gly Leu Gln Pro Ser Ala Leu Glu Leu Ala Leu Gln
            20                  25                  30

<210> SEQ ID NO 19
<211> LENGTH: 29
<212> TYPE: PRT
<213> ORGANISM: Rattus sp.

<400> SEQUENCE: 19

Glu Val Glu Asp Pro Gln Tyr Pro Gln Leu Gly Gly Pro Glu Ala
1               5                   10                  15

Gly Asp Leu Gln Thr Leu Ala Leu Glu Val Ala Arg Gln
            20                  25

<210> SEQ ID NO 20
<211> LENGTH: 31
<212> TYPE: PRT
<213> ORGANISM: Rattus sp.

<400> SEQUENCE: 20

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Ins Rodent C-peptide

<400> SEQUENCE: 21

Glu Val Glu Asp Pro Gln Val Gly Gln Val Glu Leu Gly Ala Gly Pro
1               5                   10                  15
```

Gly Ala Gly Ser Glu Gln Thr Leu Ala Leu Glu Val Ala Arg Gln
            20                  25                  30

<210> SEQ ID NO 22
<211> LENGTH: 29
<212> TYPE: PRT
<213> ORGANISM: Mus sp.

<400> SEQUENCE: 22

Glu Val Glu Asp Pro Gln Val Glu Gln Leu Glu Leu Gly Gly Ser Pro
1               5                   10                  15

Gly Asp Leu Gln Thr Leu Ala Leu Glu Val Ala Arg Gln
            20                  25

<210> SEQ ID NO 23
<211> LENGTH: 31
<212> TYPE: PRT
<213> ORGANISM: Mus sp.

<400> SEQUENCE: 23

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Gln Gln
            20                  25                  30

<210> SEQ ID NO 24
<211> LENGTH: 31
<212> TYPE: PRT
<213> ORGANISM: Cavia porcellus

<400> SEQUENCE: 24

Glu Leu Glu Asp Pro Gln Tyr Glu Gln Thr Leu Gly Met Gly Leu
1               5                   10                  15

Gly Ala Gly Gly Leu Gln Pro Leu Ala Leu Glu Met Ala Leu Gln
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Crilo C-peptide

<400> SEQUENCE: 25

Gly Tyr Glu Asp Pro Gln Val Ala Gln Leu Glu Leu Gly Gly Gly Pro
1               5                   10                  15

Gly Ala Asp Asp Leu Gln Thr Leu Ala Leu Glu Val Ala Gln Gln
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Ins Psaob C-peptide

<400> SEQUENCE: 26

Gly Tyr Asp Asp Pro Gln Met Pro Gln Leu Glu Leu Gly Gly Ser Pro
1               5                   10                  15

Gly Ala Gly Asp Leu Arg Ala Leu Ala Leu Glu Val Ala Arg Gln
            20                  25                  30

<210> SEQ ID NO 27

```
<211> LENGTH: 29
<212> TYPE: PRT
<213> ORGANISM: Artificial Sequence
<220> FEATURE:
<223> OTHER INFORMATION: Ins Ocide C-peptide

<400> SEQUENCE: 27

Glu Leu Glu Asp Leu Gln Val Glu Gln Ala Glu Leu Gly Leu Glu Ala
 1               5                  10                  15

Gly Gly Leu Gln Pro Ser Ala Leu Glu Met Ile Leu Gln
            20                  25

<210> SEQ ID NO 28
<211> LENGTH: 18
<212> TYPE: PRT
<213> ORGANISM: Mus spretus

<400> SEQUENCE: 28

Gly Gly Pro Gly Ala Gly Asp Leu Gln Thr Leu Ala Leu Glu Val Ala
 1               5                  10                  15

Gln Gln

<210> SEQ ID NO 29
<211> LENGTH: 16
<212> TYPE: PRT
<213> ORGANISM: Mus spretus

<400> SEQUENCE: 29

Gly Ser Pro Gly Asp Leu Gln Thr Leu Ala Leu Glu Val Ala Arg Gln
 1               5                  10                  15

<210> SEQ ID NO 30
<211> LENGTH: 28
<212> TYPE: PRT
<213> ORGANISM: Anas sp.
<220> FEATURE:
<221> NAME/KEY: VARIANT
<222> LOCATION: 27, 28
<223> OTHER INFORMATION: Xaa = Any Amino Acid

<400> SEQUENCE: 30

Asp Val Glu Gln Pro Leu Val Asn Gly Pro Leu Lys Gly Glu Val Gly
 1               5                  10                  15

Glu Leu Pro Pro Gln His Glu Glu Tyr Gln Xaa Xaa
            20                  25

<210> SEQ ID NO 31
<211> LENGTH: 28
<212> TYPE: PRT
<213> ORGANISM: Gallus sp.

<400> SEQUENCE: 31

Asp Val Glu Gln Pro Leu Tyr Ser Ser Pro Leu Lys Gly Glu Ala Gly
 1               5                  10                  15

Tyr Leu Pro Pro Gln Gln Glu Glu Tyr Glu Lys Val
            20                  25
```